United States Patent [19]

Pollock et al.

[11] Patent Number: 4,962,154

[45] Date of Patent: Oct. 9, 1990

[54] LATEX-ANTIGEN-ANTIBODY COMPLEXES FOR IMMUNOASSAY

[75] Inventors: Douglas K. Pollock; Charles J. McDonald; William E. Cohrs, all of Midland, Mich.; John M. Reno, Brier, Wash.

[73] Assignee: The Dow Chemical Company, Midland, Mich.

[21] Appl. No.: 218,782

[22] Filed: Jul. 14, 1988

[51] Int. Cl.$^5$ .................. C08H 1/00; C08F 12/06; C08F 20/02; C08F 20/04; C08F 20/10; C08F 22/00; C08F 120/00; C08F 122/00

[52] U.S. Cl. .................. 525/54.1; 525/329.5; 525/329.7; 525/330.3; 525/333.3

[58] Field of Search ............... 525/330.3, 333.3, 54.1, 525/329.7, 329.5

[56] References Cited

U.S. PATENT DOCUMENTS

| | | | |
|---|---|---|---|
| 4,045,384 | 8/1977 | Dorman | 524/498 |
| 4,046,723 | 9/1977 | Dorman | 524/498 |
| 4,060,597 | 11/1977 | Sato et al. | 424/12 |
| 4,080,264 | 3/1978 | Cohen et al. | 435/5 |
| 4,094,841 | 6/1978 | Mani | 524/748 |
| 4,210,723 | 1/1980 | Dorman et al. | 435/180 |
| 4,421,896 | 12/1983 | Dorman | 525/54.1 |
| 4,559,303 | 12/1985 | Aotani et al. | 435/180 |

*Primary Examiner*—Nathan M. Nutter

[57] ABSTRACT

A latex partice comprising a vinyl aromatic monomer and an vinyl acrylate ester monomer which is modified by a protein binding modifying monomer to facilitate the binding of a protein via coupling techniques. These latex particles are useful in diagnostic test applications. The vinyl acrylate ester monomer and a vinyl aromatic monomer are dispersed in a ratio between 1:3 to 3:1 of vinyl acrylate ester monomer to vinyl aromatic monomer in an aqueous phase containing a protein binding modifying monomer. The protein modifying monomer can be a vinyl carboxylic acid, such as a acrylic acid in a concentration of from about 0.5 percent to about 10 percent of the monomers. The dispersion is subjected to emulsion polymerization to provide a latex particle in a size range from 0.1 to 1 micron. The latex particle is sensitized with an antibody or antigen via coupling techniques. The resulting sensitized latex particles combine attributes of each monomer to provide utility in difficult protein systems to form latex antigen/antibody complexes. The products of the invention may be used in a variety of diagnostic applications.

17 Claims, No Drawings

LATEX-ANTIGEN-ANTIBODY COMPLEXES FOR IMMUNOASSAY

BACKGROUND OF THE INVENTION

The present invention relates to new polymeric particles useful in latex agglutination medical diagnostic applications. More particularly, the invention is directed to vinyl aromatic monomer/vinyl acrylate ester monomer copolymers, which are modified by a protein binding modifying monomer. These modified latex particles can bind a protein to the surface of the particle, and can be used to form antibody/antigen complexes used in immunoassays.

Latex particles have been used in diagnostic testing such as agglutination tests, which serve as a means to detect the presence or absence of an antibody or antigen itself. Conceptually, an antibody or antigen is bound to the surface of a latex particle which can subsequently react in body fluid, e.g., blood serum, urine and the like. Generally, the antigen bound to the latex particle is introduced to a body fluid containing the corresponding antibody. The antibody undergoes an association reaction with the antigen, forming an antibody/antigen/latex complex, which, via a bridging mechanism, aggregates with other similar complexes. These aggregates can be detected visually or by techniques which measure scattered light. This type of agglutination test is designated to detect the presence of aggregates formed, or absence of aggregates with a particular antibody. Such agglutination tests are useful for the detection of infectious agents, theraputic drugs, drugs of abuse, circulating antibodies, hormones, lipids and the like.

Latex particles used in diagnostic tests must have certain desired properties in order to function properly. For instance, the latex particles must be capable of binding an antigen to its surface, to allow the bound antigen to undergo an aggregation reaction with its corresponding antibody. The latex particle must also be insensitive or inert to other components or proteins present in the body fluid. Additionally, there must be an accurate technique for detecting the aggregation reaction.

A fundamental problem in developing latex particles for agglutination tests is not in the binding an antigen to its surface, but is preparing a particle which will specifically agglutinate in a particular body fluid. The latex particle must avoid nonspecific interaction with other serum components. If the latex particle strongly absorbs the undesirable protein components of the blood serum, then the particle would be unable to undergo specific agglutination based on an antibody/antigen reaction, or if the antibody/antigen reaction occurs, the complex does not aggregate, via a bridging mechanism, with other similar complexes. In either case, incorrect results would occur, giving either false positives or false negatives depending upon how the test is designed.

The fundamental problem in the development of latex diagnostic particles of the type described is preparing latex particles which is specifically limited to a reactive antibody or antigen, which is capable of undergoing specific agglutination in blood serum. At the present time there exists only a limited number of diagnostic tests that can be reliably made with the type of technique described. Generally, the properties of latex particles heretofore available have not been suitable for a wide range of diagnostic applications.

Thus, it is highly desirable to provide improved polymeric particles useful in latex agglutination medical diagnostic applications and having the capability of binding specific antibodies to provide improved agglutination test methods, and finding utility in a broader variety of diagnostic applications.

SUMMARY OF THE INVENTION

The present invention is a latex particle comprising a vinyl aromatic monomer and a vinyl acrylate ester monomer. The latex is prepared by dispersing vinyl acrylate ester monomer and a vinyl aromatic monomer in a weight ratio of about 1:3 to 3:1 weight percent vinyl acrylate ester monomer to vinyl aromatic monomer in an aqueous phase to form a copolymer. The copolymer is subjected to emulsion polymerization to provide a latex particle in the size range of about 0.1 to 1.0 micron.

Additionally, a protein binding modifying monomer is added to the vinyl acrylate ester and vinyl aromatic monomers in the aqueous phase, or the binding monomer can be added after polymerization of the copolymer. The protein binding modifying monomer facilitates the binding of a protein to the latex particle via protein coupling techniques known in the art, thereby sensitizing the latex particle. Typically, the coupling is done via the carbodiimide technique.

The sensitized latex particle can be treated with blood serum or other body fluids containing the corresponding antibody or antigen to form an antibody/antigen reaction. This reaction can be detected by the use of light scattering techniques known in the art and is therefore very useful in medical diagnostic applications.

Thus, another aspect of the invention is the method of treating body fluids which comprises: contacting a body fluid with a sensitized latex particle, wherein the latex particle comprises a vinyl aromatic monomer and vinyl acrylate ester monomer in a ratio of about 1:3 to 3:1 vinyl acrylate ester to vinyl aromatic monomer, whereby the sensitized latex particle and body fluid come into contact so that an antibody/antigen reaction occurs, thereby forming an antibody/antigen/latex particle complex.

An important unique and advantageous property exhibited by the latexes of the present invention is their insensitivity to extraneous protein material present in the medium in which diagnostic tests are done; e.g. blood, urine and the like. Therefore, a reliable determination of whether a particular antibody or antigen is present in the body fluid can be made.

DETAILED DESCRIPTION OF THE INVENTION

This invention involves the use of latex particles for medical diagnostic applications. The latex particles are prepared by conventional emulsion polymerization techniques. The primary components of the latex particles are a vinyl aromatic monomer, and an vinyl acrylate ester monomer. A protein binding modifying monomer which binds the protein to the particle via coupling techniques is added to the monomers when polymerizing the latex particle, or the modifying monomer can be added to the latex particle after polymerization.

The latex particle consists of a vinyl aromatic monomer and an acrylic ester monomer. The vinyl aromatic monomer can be styrene, vinyl toluene or t-butyl styrene or mixtures thereof. Preferably, the vinyl aromatic monomer can be styrene.

The vinyl acrylate ester monomer can be a monomer having pendent alkyl ester group of from 1 to 6 carbon atoms. Preferably, the vinyl acrylate ester monomer can be methyl, ethyl, propyl, n-butyl, s-butyl and other versions of the acrylate monomer or versions of a methacrylate vinyl unit, such as methyl methacrylate, ethyl methacrylate, propyl methacrylate and the like. Most preferably, the vinyl acrylate ester monomer can be n-butylacrylate.

By adding a relatively low weight fraction of a protein binding modifying monomer to the vinyl aromatic and vinyl acrylate monomers, the appropriate modification of the latex particle can be accomplished. The protein binding modifying monomer is added to facilitate the binding of the protein to the latex particle via coupling techniques known in the art. Generally, any monomer which facilitates such binding, thereby sensitizing the latex particle, can be used.

Additionally, the quantity of antibodies or antigens which can be bound to the latex particle is generally governed by the level of the protein binding modifying monomer employed into a dispersion when polymerizing the copolymer containing vinyl aromatic and vinyl acrylate ester monomer.

Typically, the protein binding modifying monomer can be a vinyl carboxylic acid. Preferably, the vinyl carboxylic acid monomer is selected from acrylic acid, methylacrylic acid, itaconic acid and fumeric acid. Most preferably, the vinyl carboxylic acid monomer is acrylic acid. Preferably, the latex particle consists of styrene, n-butylacrylate and is modified by an acrylic acid.

The latex particles of this invention are prepared by conventional emulsion polymerization methods which may include either batch or continuous addition polymerization or multiple step polymerizations. Optionally, oil-soluble or water-soluble initiators, and emulsifying agents or buffer systems to control the pH may be added. The emulsifying agent suitable for stabilizing such particles can be both ionic or nonionic emulsifiers. Of the ionic surfactant, those such as sodium dodecyl benzene sulfonate, alkyl diphenyloxide disulfonate and sodium dihexylsulfosuccinate are suitable. In these systems, water is the continuous medium and a synthetic emulsifier can be used to stabilize the particles.

In one approach, the emulsifier is of such a concentration that micelles form which solubilize a certain quantity of monomer, the majority of which is dispersed in small droplets. The addition of an initiator facilitates polymerization in these micelles which in turn imbibe more monomer. The micelles serve as the locus of polymerization of more monomer as the latter diffuses to these sites, the monomer droplets thus acting as a reservoir for this purpose.

Optionally, a seeded emulsion polymerization may be used. Here a concentration of small seed latex particles can be used as sites for further growth by the addition of more monomer. Thus, forming the latex copolymer. The temperature of the polymerization is about 70° to 95° C.

Water-soluble initiators suitable for inducing polymerization of the modifying monomer onto the copolymer can include, but are not limited to, certain inorganic oxidizing agents, such as hydrogen peroxide, sodium perborate and various per sulfates, such as sodium persulfate or potassium persulfate, preferably sodium persulfate is used. Preferably, sodium persulfate is used in the amount of about 0.1 to about 1.0 weight percent of the copolymer, preferably about 0.2 to about 0.5 weight percent.

Typically, the vinyl aromatic and vinyl acrylate ester monomers are combined in a weight ratio of about 1:3 to 3:1 vinyl acrylate ester monomer to vinyl aromatic monomer to form a copolymer. The preferred weight ratio of vinyl aromatic to vinyl acrylic ester is 1:1, based on the weight ratio of the two monomers. The protein binding modifying monomer can be attached to the particle by copolymerizing it with the bulk of the other monomers comprising the latex particle or copolymerizing it with a small fraction of the total monomer charge as, for example, a coating on the surface of a particle.

The weight fraction of the protein binding modifying monomer is defined by its efficiency with which it binds a protein. Generally, the protein binding modifying monomer is added to the copolymer in amount ranging from about 0.5 to about 10 weight percent of the copolymer. Preferably, acrylic acid is used as the protein binding modifying monomer and is preferably used in a range from about 1.0 to about 3.0 weight percent of the copolymer.

In the polymerization process the size can easily be defined by either the amount of emulsifier used or a seed particle concentration. The seed concentration is calculated as the quantity necessary to provide the preferred particle size. The particle size themselves can vary. Typically, the latex particles are about 0.1 to 1 micron, but particles in the range of 0.18–0.20 micron are preferred.

The size of the latex particle is determined primarily by the detection method to define the level of agglutination. Techniques such as elastic light scattering, quasi elastic light scattering or visible observations can define the level of agglutination. The particle size would be defined by the polymerization recipe chosen. With light scattering techniques used, the size range of the latex particle is between 0.1000 and 0.4000 micron. The preferred size of the latex particle is 0.1800 micron.

Once prepared, the desired antibody or antigen can be bound to the latex copolymer particle to form the desired latex/protein complex via an intermediate route known as the carbodiimide technique. Although the carbodiimide technique is preferred, any of the coupling techniques known in the art to facilitate the binding of the protein to a particle can be used. Carbodiimide is a group of symmetrical anhydrites of urea, having the composition HN=C=NH. The hydrogens can be substituted with other substituents to give N,N'-disubstituted carbodiimides. The acid catalyzed addition of water to these carbodiimides, i.e., hydration, to form ureas, permits the synthesis of amide and peptide bonds. Peptide bonds arise by the elimination of water, i.e., condensation between two suitably protected amino acids, one containing only a free carboxyl and the other only a free amino group, thus restricting synthesis to the formation of a specific amide bond.

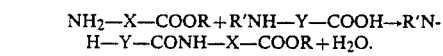

This condensation can be effected by means of dicyclohexylcarbodiimide (DCC) as taught in "A New Method for Forming Peptide Bonds", *J. Amer. Chem. Soc.*, 77 (1955) 1067-1068, Sheehan, J. C., Hess, G. P. and in "The Use of Dicyclohexylcarbodiimide in The Synthesis of Peptides", *Chem. Ind.* (London) (1955)

1087–1088, Khorana, H. G. The reaction retention is presented as follows:

where
- $R = C_6H_{11}$;
- $R'$ = the support;
- $R''$ = protein backbone;
- $CO''N$ = covalent linkage between the support and protein.

This procedure is not sensitive to moisture and can therefore be carried out in aqueous media; whereas, procedures involving mixed anhydride formation must be carried out under anhydrous conditions. The temperature and the nature of the amine and solvent influence the yield of amide, but that of the acid has little effect.

Although DCC was first used as a means for condensation, other carbodiimides have been widely used, e.g., EDC 1-ethyl-3-(3-dimethyl-aminopropyl) carbodiimide hydrochloride and CMC 1-cyclohexyl-3-(2-morpholinoethyl) carbodiimide meto-p-toluene sulphonate (FIG. 1) have been successfully used. N,N'-dicyclohexylurea, the urea formed from DCC has a very low solubility in most organic and aqueous solvents and is usually separated by crystallization. The corresponding urea derivatives of EDC and CMC however are soluble in water and are easily separated from the peptide. Therefore, EDC and CMC are preferred when a synthesis is performed in aqueous media with one reactant immobilized on a support. The synthesis is a convenient one-step procedure with no crystallizations and unreacted starting material and reaction by-products are simply washed away, leaving the antibody/antigen bound by an amide bond to a support, or as applicable in this instance, the latex particle.

The sensitized latex particles can be very useful in medical diagnostic procedures. By exposing the sensitized latex particle to body fluids- urine, blood and the like, so that the fluid comes into contact with the sensitized latex particle, an antibody/antigen reaction occurs, thereby forming an antibody/antigen/latex particle complex. Subsequently, the complex reacts with other similar complexes resulting in latex particle aggregates. To measure the occurrence of such a reaction optical techniques are used. Optical techniques can include elastic light scattering, quasi elastic light scattering and like.

In using such optical techniques, it is easiest to detect an agglutination reaction when the vinyl acrylate ester monomer concentration is low, but then the latex particle interacts non-specifically with body fluids. Conversely, when the vinyl aromatic monomer concentration is low, the latex particle does not readily interact non-specifically with the body fluids, but the aggregation reaction is difficult to detect. Thus, by taking into account the need for easy detection of the agglutination reaction and the need for the latex particle to be inert to non-specific interaction with the body fluids, the weight ratio of 1:1 vinyl acrylate ester monomer to vinyl aromatic monomer is therefore preferred.

EXAMPLES

Typical examples of the method of the invention are set forth below. These examples are intended to be illustrative only and are not to be construed in any limiting sense.

A

Preparing the Latex Particle

280 Grams (g) of deionized water plus 1.9 grams of a 300 Å seed polystyrene are added to a 1 liter flask fitted with a thermowell and half moon agitator rotated at 300 rpm and purged with prepurified nitrogen for 10 minutes to remove oxygen.

Two separate reagents are made and are added to a reaction flask at a consistent rate over a three hour period of time, one reagent containing water-soluble ingredients, and the other the monomer mixture.

| Aqueous Reagent | Monomer Reagent |
|---|---|
| 160 g of dionized water purged with nitrogen | 194 g of styrene (1.2 ppm TBC) |
| 2 g of sodium persulfate (initiator) | 194 g of n-butyl acrylate 15 ppm (MEHQ) |
| 1 g of sodium bicarbonate (buffer) | 12 g of acrylic acid (MEHQ) |
| 4 g of DOWFAX* 2A1 (51.3 percent active) | Purged nitrogen 10 minutes |

*Trademark of The Dow Chemical Company

The temperature was held constant at 90° C. +/−0.5° C. during addition of the two reagents. The polymerization was essentially a "semi-continuous" addition and produced a theoretically instantaneous composition, with no initial charge compensation.

The product obtained in the above procedure is characterized by the following values of the several parameters. The solids content of the final latex was between 46.5 and 47.0 grams (g), or greater than 97 percent conversion of the monomer. The product included particles in the size range of 0.1800 microns to 0.1900 microns as determined by electron microscopy, or a method based on size exclusion chromatography known as hydrodynamic chromatography.

The surface acid level is found to be 1.5 percent parts per 100 parts polymer, after removing extraneous water phase acrylic acid containing moieties, by an ion exchange resin (mixed bed). This latex clean-up is an accepted procedure in measurement of bound acid in such modified particles.

The above example illustrates the preparation of the 50/50 weight fraction latex particles, 50 styrene/50 n-butyl acrylate. Other combinations of the latex particle are prepared as described above, except the weight ratio is varied. The combinations are made as described above and are used in Example Parts B, C and D.

| Variation | Weight Ratio of Styrene to N-Butyl Acrylate |
|---|---|
| 1 | 90/10 |
| 2 | 75/25 |
| 3 | 60/40 |
| 4 | 55/45 |
| 5 | 50/50 |

B

Extent of Serum Interaction with the Latex Copolymer Particles

An accurate valve of the quantity of active protein bound to the particle can be determined with the use of radioactive tracers. Such data indicates that the quantity of reactive protein that can be bound is equivalent for all copolymer particles, independent of the vinyl acrylate ester monomer and vinyl aromatic monomer ratio.

By measuring the electrokinetic mobility of particles to which a protein is bound, it is feasible to establish the relative sensitivity of the surface of the latex particles in buffer to blood serum. Significant changes in the mobility in the presence of serum would indicate adsorption on the surface of the particle.

TABLE I

| Electrokinetic Mobility Data | | |
|---|---|---|
| Polystyrene | Human Chorionic Gondrotripin in buffer | 2.81 |
| Polystyrene | Human Chorionic Gondrotripin in Human Serum | 1.42 |
| Latex Copolymer 50/50 (S/nBA) | Human Chorionic Gondrotripin in buffer | 2.13 |
| Latex Copolymer 50/50 (S/nBA) | Human Chorionic Gondrotripin in Human Serum | 1.92 |

As seen in Table I, there is a significant change in the electrokinetic mobility between polystyrene in the buffer solution and in human serum which indicates an undesirable interaction between polystyrene and other serum components. Whereas, there is little change in the electrokinetic mobility between the 50/50 polystryene/n-butylacrylate copolymer in the buffer solution and in human serum. Therefore, this lack of change indicates a negligible amount of undesirable interaction between the acrylate copolymer and other serum components.

More significant evidence of the unique serum insensitivity of the acrylate-based particles of the invention is contained in Tables II and III.

C

Latex Particles' Inhibition by Serum

Table II presents data on the relative reactivity of the particles to agglutinate as a function of serum concentration. The particles have a constant level of antigen present on the surface as determined by their reactivity to the antibody in buffer. As the concentration of serum increases, the inhibition of the agglutination is variable depending upon particle composition.

TABLE II

| | Percent Inhibition of Agglutination | | | | |
|---|---|---|---|---|---|
| Monomer Ratio (S/nBA) (%) Serum | Ex. A-1 (%) 90/10 | -2 (%) 75/25 | -3 (%) 60/40 | -4 (%) 55/45 | -5 (%) 50/50 |
| 0 | 0 | 0 | 0 | 0 | 0 |
| 0.5 | 59 | 25 | 18 | 5 | 5 |
| 1.0 | 86 | 43 | 25 | 10 | 5 |
| 2.0 | 92.5 | 54 | 27 | 13 | 3 |
| 5.0 | 100 | 73 | 25 | 10 | 3 |
| 10.0 | 100 | 88 | 26 | 10 | 0 |

Thus, as observed in Table II, as the weight percent of acrylate increases, the percent of inhibition of agglutination decreases. At a particle composition of equal weights of styrene and n-butylacrylate, the serum effect is negligible.

D

Detection of Agglutination by Latex Particle

The extent of agglutination is measured by light scattering which is sensitive to the refractive index of the particle components. Table III sets forth data on the reactivity of the copolymer particles in buffer as a function of the concentration of antibody and is described in terms of the rate of increase of the light scattered from the dispersed system. As agglutination occurs, the particles aggregate and scatter more light. The antigen concentration on the surface of the particles is the same for all particles. Additionally, the reactivity of the antigen-/antibody binding in buffer is the same, but the ability to detect aggregation is maximized when the concentration of styrene in the particle is highest. This is related to the higher refractive index of the styrenic polymer.

TABLE III

| | Reactivity in Buffer Rate Change Scatter Light (volts/cm) | | | | | |
|---|---|---|---|---|---|---|
| Monomer Ratio (S/nBA) Antibody Conc $C_0 1/2^n$ | Ex. A-1 90/10 | -2 75/25 | -3 60/40 | -4 55/45 | -5 50/50 | * 10/90 |
| n = 3 | 3.4 | 3.2 | 2.30 | 1.62 | 0.95 | 0.07 |
| n = 4 | 2.65 | 2.47 | 1.81 | 1.28 | 0.72 | 0.05 |
| n = 5 | 1.80 | 1.67 | 1.38 | 0.90 | 0.38 | 0.02 |
| n = 6 | 0.92 | 0.85 | 0.70 | 0.40 | 0.13 | — |
| n = 7 | 0.43 | 0.375 | 0.32 | 0.17 | 0.07 | — |

*Outside the scope of the invention.

As seen in Table III, the agglutination is easily detected when the acrylate monomer concentration of the latex particle is low, 90/10 styrene to n-butyl acrylate. Since the serum inhibition is maximized when the particles consist primarily of styrene, an intermediate composition, 50/50 ratio of copolymers, is used in the practice of the present invention, to balance the serum insensitivity and the detectability of the agglutination reaction.

What is claimed is:

1. A latex particle comprising a vinyl aromatic monomer selected from the group consisting of styrene, vinyl toluene, t-butyl styrene and mixtures thereof, a vinyl acrylate ester monomer having a pendent alkyl ester group of from 1 to 6 carbon atoms, wherein the vinyl aromatic monomer and vinyl acrylate ester monomer are employed in a weight ratio of about 1:3 to 3:1 vinyl acrylate ester to vinyl aromatic monomer, and a protein binding modifying monomer which is a vinyl carboxylic acid that is about 0.5 to about 10 weight percent of the vinyl aromatic and vinyl acrylate ester monomers.

2. A latex particle as in claim 1, wherein the vinyl aromatic monomer and vinyl acrylate ester monomer are employed in a ratio about 1:1.

3. A latex particle as in claim 1, wherein the vinyl acrylate ester is selected from the group consisting of methacrylate, n-butylacrylate, s-butylacrylate and mixtures thereof.

4. The latex particle as in claim 1, wherein the vinyl carboxylic acid is selected from the group consisting of acrylic acid, methylacrylic acid, and mixtures thereof.

5. The latex particle of claim 1, wherein the protein binding modifying monomer is employed in a concentration of about 1.0 to 3.0 weight percent of the copolymer.

6. The latex particle as in claim 1, wherein the said latex particle is about 0.1 to 1.0 micron.

7. The latex particle as in claim 1, wherein said latex particle is about 0.1800 micron to about 0.2000 micron.

8. A latex particle comprising a n-butylacrylate monomer and styrene monomer in a ratio of about 1:3 to 3:1 n-butylacrylate monomer to styrene monomer, which forms a copolymer and is used in diagnostic immunoassay applications.

9. The latex particle as in claim 8, wherein the n-butylacrylate monomer and styrene monomer are combined in a weight ratio of about 1:1.

10. The latex particle as in claim 9, wherein the latex particle is further modified by a protein binding modifying monomer which via coupling techniques, binds a protein to the latex particle, thereby sensitizing the latex particle so that said sensitized latex particle is used in diagnostic immunoassay applications.

11. The latex particle as in claim 10, wherein the protein binding modifying monomer is a carboxylic acid.

12. The latex particle as in claim 10, wherein the protein binding modifying monomer is employed in a concentration of about 0.5 to 10.0 weight percent of the copolymer.

13. The latex particle as in claim 12 wherein the protein binding modifying monomer is employed in a concentration of about 1.0 to 3.0 weight percent of the copolymer.

14. The latex particle as in claim 10, wherein said latex particle is about 0.1 to 1.0 micron.

15. The latex particle as in claim 14, wherein said latex particle is about 0.18 to 0.20 micron.

16. A latex particle comprising a vinyl aromatic monomer, a vinyl acrylate ester monomer and a protein binding modifying monomer, wherein said protein binding modifying monomer which is a vinyl carboxylic acid couples a protein to said latex particle, thereby sensitizing the latex particle so that said latex particle is used in diagnostic immunoassay applications.

17. The sensitized latex as in claim 16, wherein the protein is coupled to the latex particle via the carbodiimide technique.

* * * * *